May 28, 1968 P. ECKE Plant Pat. 2,812
POINSETTIA PLANT
Filed Feb. 2, 1967
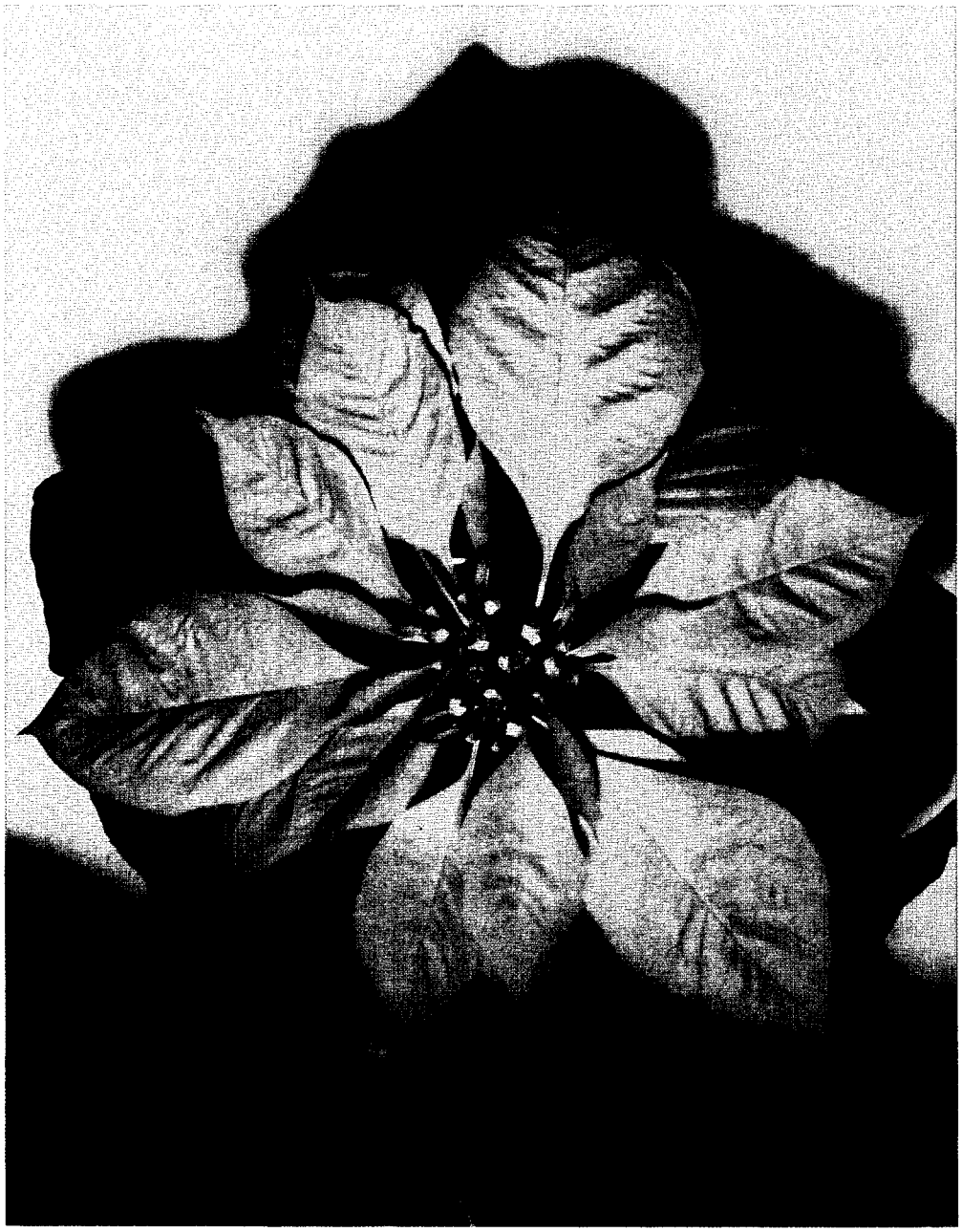
Inventor.
Paul Ecke
By: Robb & Robb
Attorneys.

United States Patent Office

Plant Pat. 2,812
Patented May 28, 1968

2,812
POINSETTIA PLANT
Paul Ecke, P.O. Box 488, Encinitas, Calif. 92024
Filed Feb. 2, 1967, Ser. No. 613,687
1 Claim. (Cl. Plt.—86)

The present invention relates to a new and distinct variety of poinsettia plant (botanically known as *Euphorbia pulcherrima*), which was originated by me by crossing the variety known as "Elisabeth Ecke" (Plant Patent No. 2,243) with the variety known as "Ecke's White" (Plant Patent No. 1,802), the former being the seed parent and the latter being the pollen parent.

The primary objectives of this breeding were to produce a new and improved poinsettia variety which has stiff stems and does not require staking, which retains its bracts and foliage for an unusually long period of time after reaching maturity, and a plant which, in general, was more attractive than other varieties heretofore known in commerce. These objectives were fully achieved, along with other desirable features, as evidenced by the following unique combination of characteristics which are outstanding in the new variety and which distinguish it from its parents, as well as from all other varieties of which I am aware:

(1) A very vigorous, tough and durable plant habit;
(2) Stiff stems which do not require staking;
(3) A very vigorous and extensive root system;
(4) More bracts than other known poinsettia varieties of the long-lasting, stiff stem types, said bracts being produced in an unusually large number and having short petioles which give a more attractive fullness to the plant;
(5) Retention of the bracts, foliage and inflorescences for an unusually long period of time after reaching maturity;
(6) A normally later blooming habit, but having the ability to be satisfactorily brought into bloom and full maturity in every month of the year through the exercise of proper greenhouse cultural techniques;
(7) A distinctive and attractive slightly ruffled appearance of the bracts and their absence of any tendency to droop with age;
(8) A distinctive and attractive general color tonality of the bracts corresponding to Delft Rose;
(9) Absence of drooping and retention of the inflorescence position relative to the bracts without rising as occurs in other varieties as the inflorescence approaches maturity;
(10) A suitability for the production of multiple bloom plants; and
(11) Excellent keeping qualities and consequent suitability for home decoration.

Asexual reproduction of my new variety by vegetative cuttings propagated under mist at Encinitas, Calif., shows that the foregoing characteristics and distinctions come true to form and are established and transmitted through succeeding propagations.

The accompanying drawing shows a typical specimen plant of my new variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Encinitas, Calif., under regular commercial practices:

Parentage: Seedling.
*Seed parent.*—"Elisabeth Ecke."
*Pollen parent.*—"Ecke's White."

Propagation: Holds its distinguishing characteristics through succeeding propagations by vegetative cuttings.
Form: Medium tall; upright.
Habit of growth: Vigorous; medium upright.
Rooting habit: Vigorous; extensive; uniform.
Blooming habit: Normal.
Blooming season: Can be satisfactorily brought into bloom in every month of the year by appropriate greenhous culture practices.
Foliage: Alternate; borne horizontally on stems; persistent; normal quantity.
*Size.*—Medium (from about 3 inches to 7 inches long); width from about 2½ inches to 4 inches.
*Shape.*—Both serrated and nearly oval.
*Texture.*—Upper side—semi-glossy; ordinary recessed veins. Under side—dull; ordinary protruding veins.
*Margin.*—Well defined.
*Color.*—New foliage:—upper side—near Scheele's Green, Plate 860, page 175; lower side—near Scheele's Green, Plate 860/1, page 175. Old foliage:—upper side—near Spinach Green, Plate 0960, page 187; lower side—near Spinach Green, Plate 0960/3, page 187.
Disease resistance: Resistant to rhizoctonia and pythium stem and root rot during propagation and growing period, and resistant to botrytis during blooming period, as determined by comparison with other plants grown under the same cultural conditions at Encinitas, Calif., which are infected with these diseases.
Bracts: Many (approximately 20 to 25 in number); wide; excellent retention; new bracts form and develop as other bracts mature; very long lasting qualities; short pointed when young, but becoming long pointed at maturity; retain relative position and do not droop when mature or as bracts continue to age; retain their color exceptionally well; slightly ruffled in appearance; have short petioles giving a full appearance. Color:—upper side—from near Delft Rose, Plate 020, page 108 to Delft Rose, Plate 020/2, page 108; under side—near Rose Opal, Plate 022/1, page 110.
Flowers:
*Borne.*—Continuously for several months; many flowers per stem in regular clusters in varying stages of development; borne on strong, short stems; slow development, giving a compact appearance for a greater period of time; position of flowers remains relatively low without rising as it does in other commercial poinsettia varieties during early development, and does not spread out during later stages of development, thereby giving a more attractive appearance for a longer period of time.
*Quantity of bloom.*—Relatively abundant; continuous; flowers gradually drop off after maturity but new ones continue to develop as flower stems continue to grow.
*Buds.*—From small to medium size; borne on light green stems. Color—near Lettuce Green, Plate 861/3, page 176.
Reproductive organs:
*Stamens.*—Few; from about ⅛ inch to ¼ inch long. Color—near Claret Rose, Plate 021, page 109.
*Pollen.*—Color—near Naples Yellow, Plate 403, page 121.
*Styles.*—Color—near Rose Opal, Plate 022, page 110.
*Ovaries.*—Color—near Lettuce Green, Plate 861/2, page 176.
*Nectar cups.*—Color—near Egyptian Buff, Plate 407, page 122.

General observations: There is no real comparison of the new variety with either parent, although the new variety is similar in form, but has red bracts as compared with the pollen parent "Ecke's White," and the new variety is shorter than this parent variety. In comparison with the seed parent "Elisabeth Ecke," the new variety has stiffer stems, has better leaf and bract retention, is faster rooting, and the center of the inflorescence is more compact.

I claim:

1. A new and distinct variety of poinsettia plant, substantially as herein shown and described, characterized particularly as to novelty by the unique combination of a very vigorous, tough and durable plant habit, stiff stems which do not require staking, a very vigorous and extensive root system, more bracts than other known poinsettia varieties of the long-lasting, stiff stem types, said bracts being produced in an unusually large number and having short petioles which give a more attractive fullness to the plant, retention of the bracts, foliage and inflorescences for an unusually long period of time after reaching maturity, a normally later blooming habit, but having the ability to be satisfactorily brought into bloom and full maturity in every month of the year through the exercise of proper greenhouse cultural techniques, a distinctive and attractive, slightly ruffled appearance of the bracts, and their absence of any tendency to droop with age, a distinctive and attractive general color tonality of the bracts corresponding to Delft Rose, absence of drooping and retention of the inflorescence position relative to the brats without rising as occurs in other varieties as the inflorescence approaches maturity, a suitability for the production of mutiple bloom plants, and excellent keeping qualities and consequent suitability for home decoration.

No references cited.

ROBERT E. BAGWILL, *Primary Examiner.*